United States Patent [19]

Reipa et al.

[11] Patent Number: 5,453,841
[45] Date of Patent: Sep. 26, 1995

[54] METHOD FOR THE DYNAMIC MEASUREMENT OF THE PROGRESS OF A CHEMICAL REACTION OF AN ELECTROCHEMICAL INTERFACE

[75] Inventors: Vytautas Reipa; Adolfas K. Gaigalas, both of Gaithersburg, Md.

[73] Assignee: The United States of America as represented by the Secretary of Commerce, Washington, D.C.

[21] Appl. No.: 55,383

[22] Filed: May 3, 1993

[51] Int. Cl.$^6$ .................................................. G01N 21/47
[52] U.S. Cl. ........................ 356/445; 356/446; 356/448
[58] Field of Search .................................. 356/445, 446, 356/447, 448, 345; 422/82.07, 82.08; 436/34, 165, 172

[56] References Cited

U.S. PATENT DOCUMENTS

| | | |
|---|---|---|
| 3,857,637 | 12/1974 | Obenreder . |
| 3,975,084 | 8/1976 | Block ........................................ 356/244 |
| 4,233,664 | 11/1980 | Grandchamp ............................ 356/336 |
| 4,621,063 | 11/1986 | Wyatt et al. ............................. 356/371 |
| 4,652,755 | 3/1987 | Solomon et al. ........................ 356/442 |
| 4,670,113 | 6/1987 | Lewis ........................................ 704/80 |
| 4,685,806 | 8/1987 | Arnberg . |
| 4,853,777 | 8/1989 | Hupp . |
| 4,866,287 | 9/1989 | Weber . |

FOREIGN PATENT DOCUMENTS

| | | |
|---|---|---|
| 766225 | 1/1984 | U.S.S.R. . |
| 1375953 | 2/1988 | U.S.S.R. . |

OTHER PUBLICATIONS

*J. Electroanal. Chem.*, 328 (1992), pp. 99–110 (1992), Gaigalas et al., "Observation of photon correlations in scattering from a silver electrode".

*Primary Examiner*—Richard A. Rosenberger
*Assistant Examiner*—Robert Kim
*Attorney, Agent, or Firm*—Stevens, Davis, Miller and Mosher

[57] ABSTRACT

A method for the dynamic measurement of the progress of a chemical reaction at an electrochemical interface. The method comprises: applying a direct coherent light to a solid interface within a sample in which the chemical reaction is occurring; measuring a scattering of the light after it contacts the electrode; and autocorrelating the scattering information with previously obtained scattering information for the electrode. This method allows the measurement of the progress of the chemical reaction to be made in situ, without removing the solid interface from the sample or stopping the chemical reaction. The coherent light source is, for example, a laser such as a low power helium-neon laser and a solid state laser. The chemical reaction measured can be, for example, metal finishing, electrochemical machining, corrosion protection, metal deposition, electrochemical production, waste water treatment or electrowining.

20 Claims, 11 Drawing Sheets

METHOD FOR THE DYNAMIC MEASUREMENT OF THE PROGRESS OF A CHEMICAL REACTION OF AN ELECTROCHEMICAL INTERFACE

FIELD OF THE INVENTION

The present invention relates generally to a method of measuring the progress of a chemical reaction occurring at an electrochemical interface. Specifically, the present invention relates to a method which allows real time measurement of the progress of a chemical reaction. The present method utilizes a coherent light source for the direct, in situ measurement of the progress of the reaction due to changes in surface roughness and surface polarizability.

BACKGROUND OF THE INVENTION

Although electrolytic deposition or dissolution of metals have been extensively studied, the mechanisms thereof remain polemic. This is partly due to the fact that kinetic models imply reaction intermediates or products whose existence or nature are still questionable. Usual questions in dissolution are whether a layer is involved and does removal of products of the anodic reaction proceed by convective diffusion through an homogeneous liquid medium of space-varying physical properties (viscosity, difffusivity and the like) or in a nonhomogeneous liquid with solid particles.

Despite the now well-established conditions between the electrode roughness and the nature of the electrochemical control (diffusion/reaction) and the recent progress in electrocrystallization and mass transport in electrolytic solutions, there is still a lack of sensitive in situ methods for the detection and measurement of small particles near the electrode surface. Most measurements of particles are conducted by visual observation through the optical microscope, double layer capacitance monitoring or ex situ particle analysis.

That is, prior to the present invention, it was known to measure the progress of a chemical reaction occurring at an electrochemical interface only in an indirect manner. Techniques of measuring surface roughness, but not during a chemical reaction, using a reflected light source and ex situ techniques (not real time measurements) are known. See for example, U.S. Pat. Nos. 3,857,637 to Obenreder; 4,685,806 to Arnberg; 4,853,777 to Hupp; 4,866,287 to Weber; SU 1375-953 to Chely Metal Wks; and SU 766-225 to Mosc Aviation Inst, the disclosures of which are herein incorporated by reference. However, nothing in the prior art discloses or suggests a real time, direct measuring method, as disclosed herein.

SUMMARY OF THE INVENTION

An object of the present invention is to provide a method of monitoring electrochemical interfaces (such as a solid-liquid or solid-gas interface) in situ, using real time dynamic measurements.

This object is achieved by the present invention, which relates to a method for electrolytic particle detection utilizing dynamic light scattering, which is both sensitive and informative.

BRIEF DESCRIPTION OF THE DRAWINGS

FIG. 2b shows the Fourier transform of the autocorrelation spectrum shown in FIG. 2a.

DETAILED DESCRIPTION OF THE INVENTION

The present invention can characterize the dynamic surface roughness due to deposition or dissolution on a time scale of a second. Changes in surface polarizability resulting from passivation activation dynamics can be seen on a millisecond time scale. Particles of insoluble reaction products can be detected in the initial phase of formation. The apparatus, the reacting interface, and the interpretation of the measurement constitute a novel application which is central to the invention.

Traditionally, the monitoring of electrochemical interfaces has been accomplished using indirect methods. Weight loss analysis of the electrode is used in processes utilizing anodic dissolution such as metal finishing, electrochemical machining and corrosion protection. Solution analysis and monitoring of charge and current are used in processes involving metal deposition, electrochemical production, and waste water treatment. These methods are mostly ex situ, not in real-time, and do not contain direct information about the condition of the electrode surface. Dynamic light scattering has not been applied to this problem.

The present inventors first reported the observation of photon correlations in scattering from a silver electrode in Gaigalas et al, *J. Electroanal. Chem.*, vol. 328, pages 99–110 (1992), the disclosure of which is incorporated herein.

Figure 1:
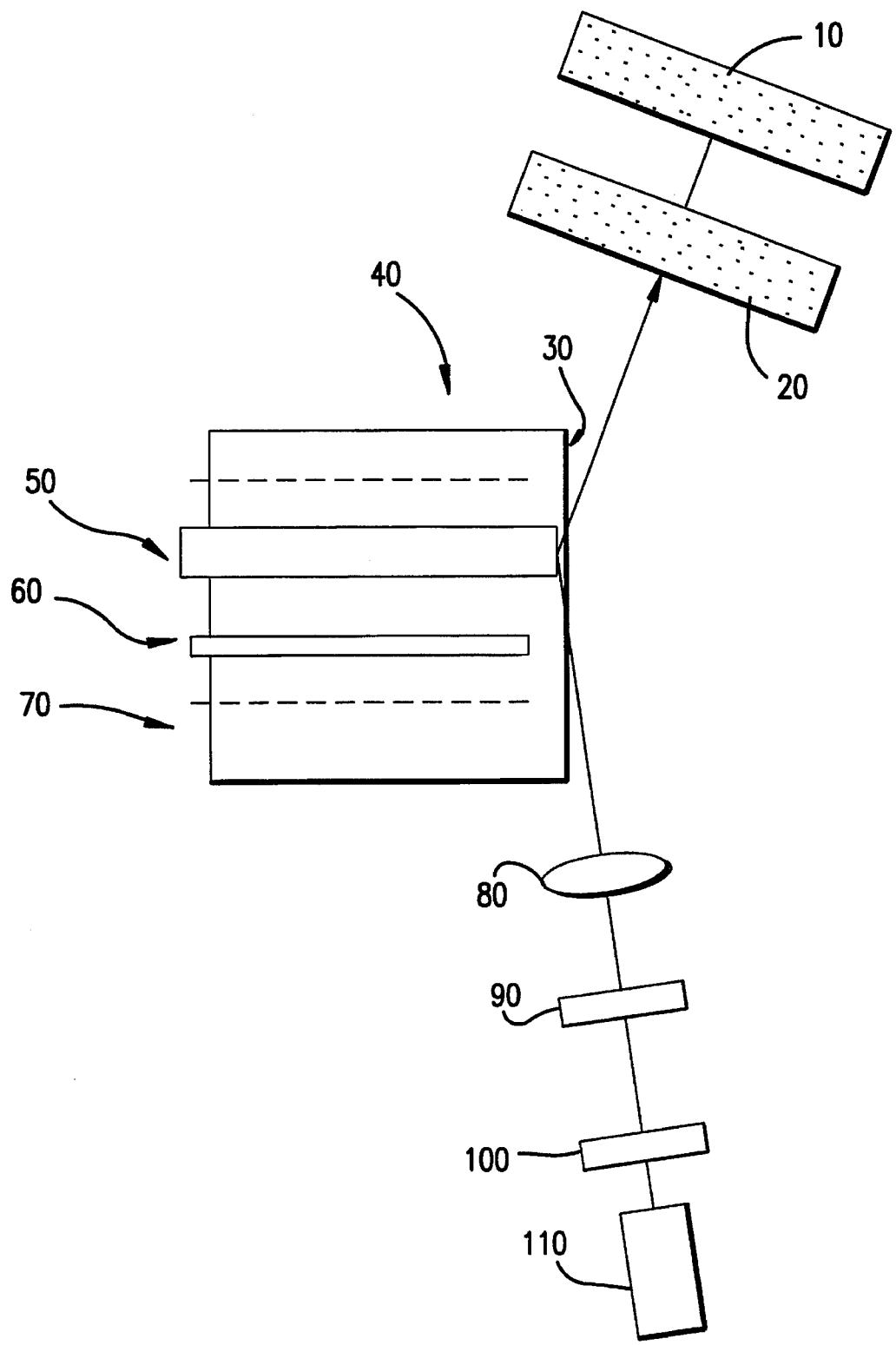
FIG. 1 is a schematic of an experimental apparatus used in the present invention, which measures the autocorrelation spectrum of photon scattering from the electrode surface.

At least two different optical arrangements can be used in the present invention, as shown in FIG. 1, in which 10 indicates an autocorrelator, 20 indicates a detector, 30 indicates a window, 40 indicates a sample cell wall, 50 indicates a silver electrode, 60 indicates a reference electrode, 70 indicates an auxiliary electrode, 80 indicates a lens, such as a focusing lens, 90 indicates a filter, such as a neutral density filter, 100 indicates a polarizer and 110 indicates a coherent light source, such as a laser. Both arrangements comprise a coherent light source, means for directing the coherent light source so as to impinge, at an angle of incidence (relative to normal), upon a solid-liquid interface undergoing chemical reaction, a detector which detects photons scattered from the impingement of the coherent light source upon said interface undergoing chemical reaction, and means for generating an output from said detector, and means for determining the progress of the chemical reaction from the output of the detector.

Figure 2A:
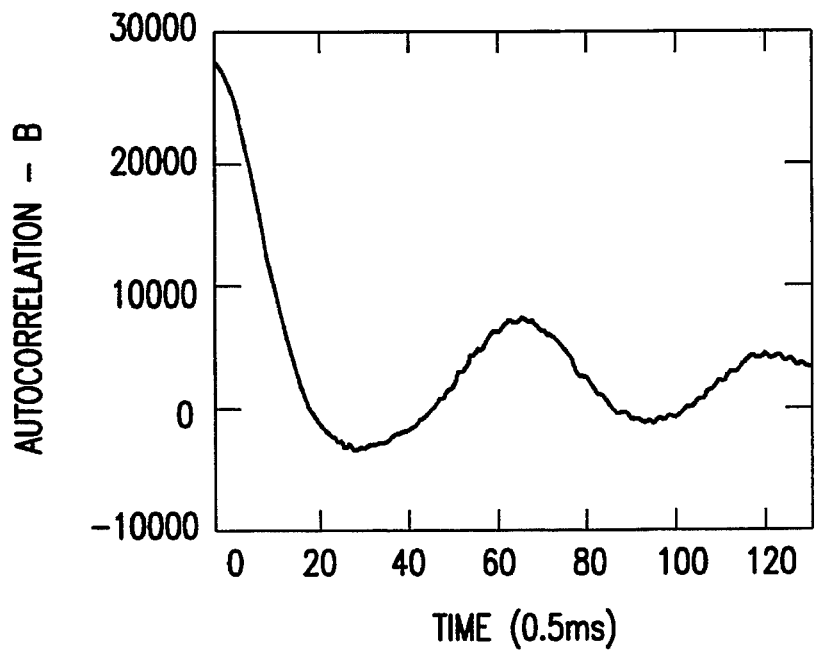
FIG. 2a is the measured autocorrelation spectrum of photons scattered from alumina particles having a density of 2.2 g/cc and a mean diameter of 5.9 microns settling in water.
Figure 2B:
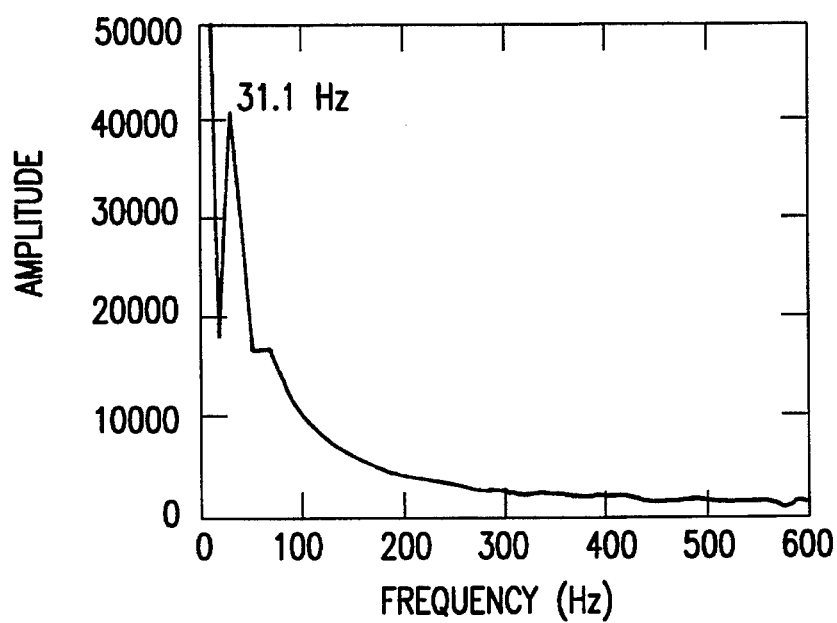

In the first, a horizontal electrode surface, facing down, was illuminated by a laser beam at an angle of incidence (relative to the normal) of 80 degrees. Scattered photons were detected at an angle approximately 75 degrees to the normal. This geometry provided a scattering vector perpendicular to the electrode surface. The incident beam was partially focused so as to illuminate the electrode in a large well defined area. The detection optics had a spatial filter which was adjusted to detect photons originating from a smaller portion of the illuminated area. Such an arrangement minimized detected intensity fluctuations arising from the movement of the illuminated area on the electrode surface relative to the sensing area. The illuminated area can move due to the inherent laser beam angular fluctuations, vibrations of optical elements used to guide the incident beam, and vibrations of the electrode housing. The above mentioned intensity fluctuations were not detected during the tests with the electrode surface in air. The scattering arrangement described above allows the measurement of uniform motion of particles perpendicular to the electrode surface (direction of gravity). Interference of scattered light from the surface and the falling particles produces beats whose frequencies are proportional to the particle velocity. The proportional factor with this arrangement is 1.1 micrometer.s$^{-1}$/Hertz. A test was performed by replacing the electrode with a cuvette filled with a solution containing alumina particles having a mean diameter of 5.9 micrometers. The optics were adjusted to include scattered photons both from the cuvette wall and the particles. FIG. 2a shows the measured autocorrelation spectrum. The beat frequency of 31 Hertz is in the range of that expected for motion under gravity (23 Hz) as given by the Stokes formula and considering a particle density of 2.2 g/cm$^3$. The discrepancy probably arises from the uncertainty in the value of the particle radius as the velocity depends on the radius squared.

In the second optical arrangement, the electrode surface was set as close as possible to a vertical position while the incident and the observation beams formed a horizontal plane thus insensitive to the settling of particles. Such an arrangement is thus aimed at measuring only the diffusion coefficient of the particles.

Measurements were performed in solutions containing different concentrations of the mixture $KAg(CN)_2/KCN$, i.e., concentrations of 0.1M/0.1M (pH=11.1), 0.05M/0.05M (pH=10.9), and 0.1M/0.5M (pH=11.3). A 6 mm diameter silver rod (Johnson-Matthey), embedded in Teflon, with one end exposed was used as a working electrode. The working electrode was successively polished with emery paper and alumina suspension, then washed with distilled water and sonicated for 5 minutes before every experiment to avoid interfering alumina particle release during the experiments. A Pt counterelectrode was positioned around the working electrode while AgCl reference was isolated by a salt bridge. Before the experiments, solutions were deaerated by bubbling Ar gas for 15 minutes. Current and potential control was provided by PAR 173 potentiostat/gavanostat.

Figure 3:
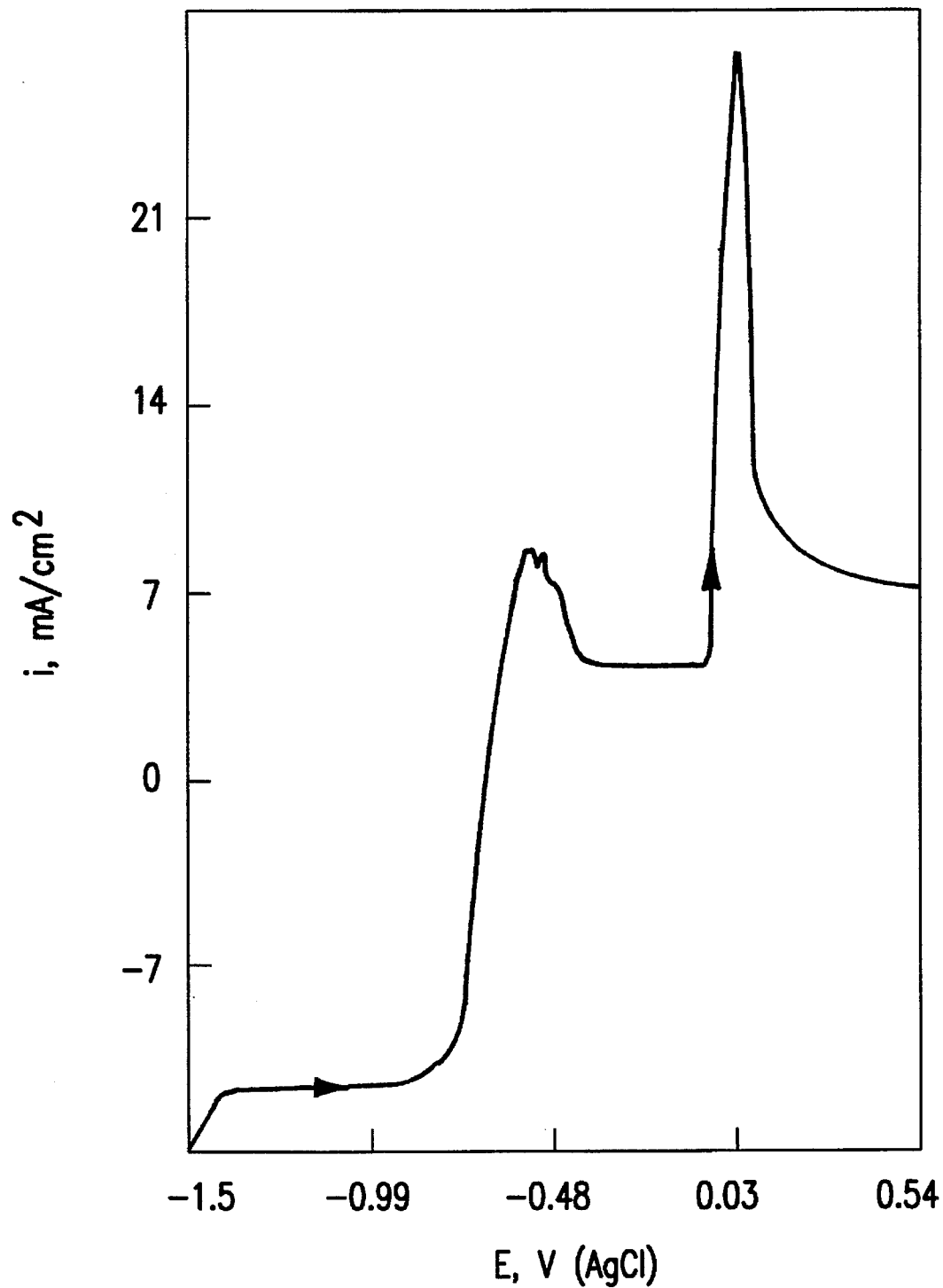
FIG. 3 is a polarization curve for a silver electrode in a solution containing 0.1M KCN and 0.1M $KAg(CN)_2$ at pH=11.
Figure 4:
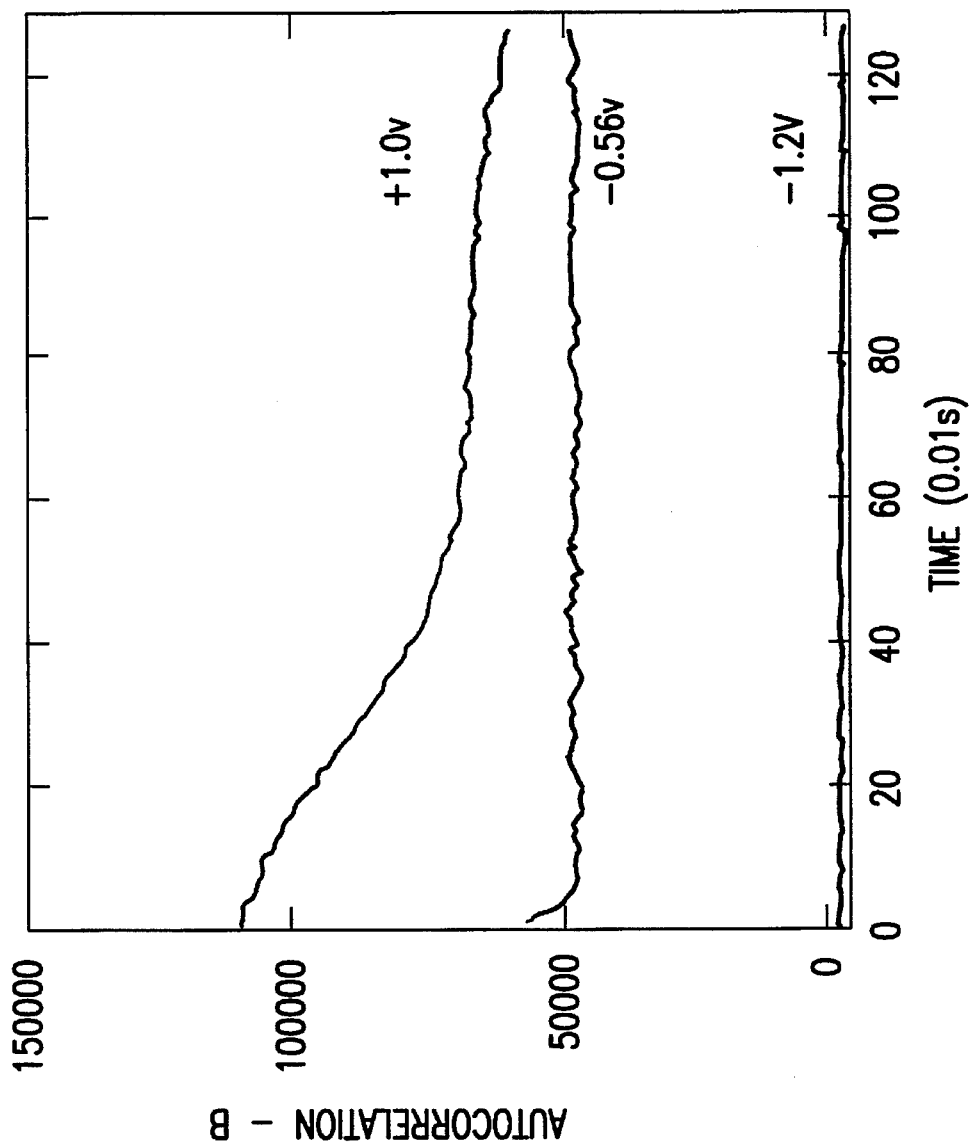
FIG. 4 is the measured autocorrelation spectra for three potentials of the silver electrode in 0.1M KCN and 0.1M $KAg(CN_2$ at a pH=11.1.

The voltammogram (FIG. 3) measured at a scan speed 3 mV/s between −0.5 and +0.5 V consists of a cathodic reduction wave and two anodic current peaks. The autocorrelation spectra were taken at several fixed potentials corresponding to either open circuit conditions, dissolution or deposition. FIG. 4 shows an example of autocorrelation spectra taken in the open circuit (−0.56 V), on deposition plateau (−1.2 V) or while dissolution is underway at +1 V. That is, dissolution and deposition is obtained at +1.0 V and −1.2 V respectively, while −0.56 V corresponds to the open circuit potential. There is a large time dependence in the autocorrelation spectrum taken during dissolution, while very little time dependence is observed for the other two cases. The main common features shown here are present in the 3 investigated solutions and correspond to the case of horizontal electrodes. Only measurements on the dissolution plateau contain significant correlation which can be clearly assigned to the presence of particles released from the electrode surface.

In contrast, the same measurements in dissolution but at a vertical electrode display only an exponential decay, or no change in scattering for open circuit and deposition conditions.

When the interface is a solid-gas interface, the gas contains species which react with the solid. The system would lead to changes in the surface roughness and polarizability as well as the production of particles.

Analysis of Scattered Light

For the purposes of this analysis, there are two sources of scattered photons. The first is the surface and the second source is particles adjacent to the surface. The intensity of photons scattered from the surface and the particles will be denoted by $I_s$ and $I_p$ respectively. Assuming that the scattering from the surface and the particles is uncorrelated, the measured photon autocorrelation function can be written as:

$$G(t)=<I_s(t)I_s(0)>+2<I_sXI_p<+>I_p(t)I_p(0)>+2Re[I_{p1}(t)I_{s1}(t)]$$

where $$I_{s1}(t)=<E_s^*(t)E_s(0)>$$

$$I_{p1}(t)=<E_p^*(t)E_p(0)>$$

Here $E_s$ and $E_p$ are the scattered electric fields at the detector.

If the assumption is made that the scattered fields are Gaussian random variables, then the intensity autocorrelation can be written in terms of the electric field autocorrelation as:

$$<I_p(t)I_p(0)>=|I_{p1}(0)|^2=|I_{p1}(t)|^2$$

with a similar expression for the surface field. To continue further, it is necessary to introduce specific mechanisms for the scattering. A plausible cause of surface scattering is variation of surface roughness and reflectivity which leads to a field autocorrelation of the form:

$$I_{s1}(t)=A \exp(-G_1T)=B \exp(-G_2t)$$

Figure 5A:
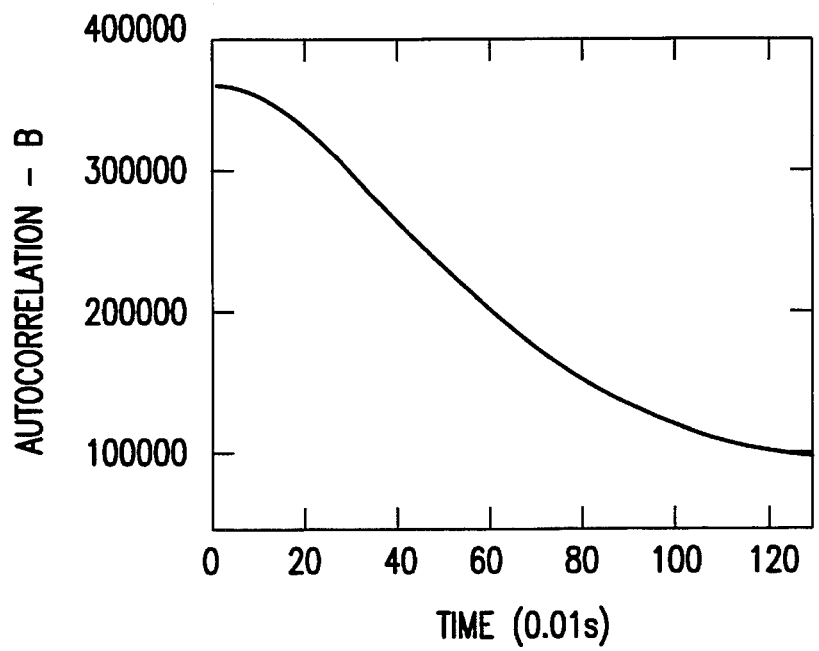
FIG. 5a is the measured photon autocorrelation spectrum for a silver electrode in a solution containing 0.1M KCN+ 0.1M $KAg(CN)_2$, at a potential of −0.1 V.
Figure 5B:
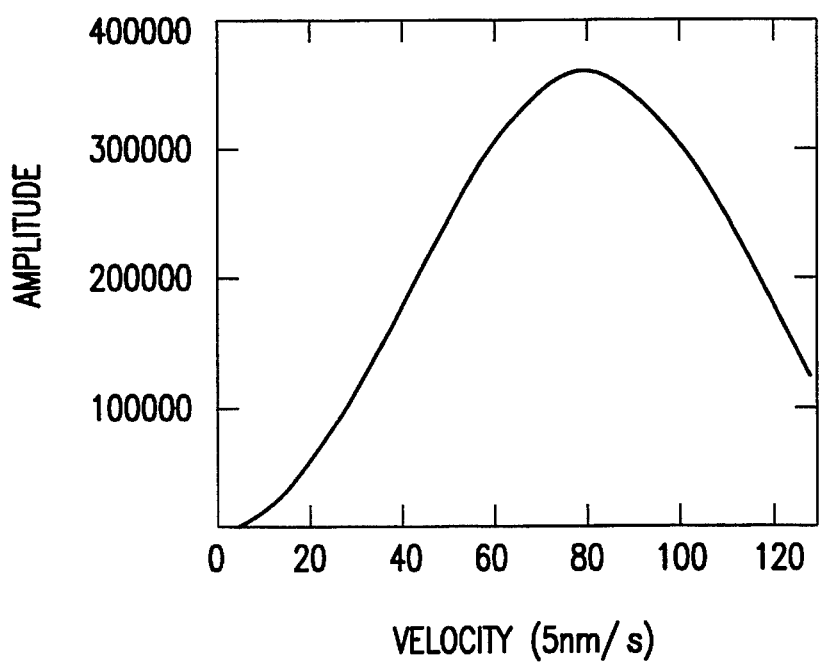
FIG. 5b shows the velocity distribution obtained from the data in FIG. 5a, assuming the particles are the same size, the average velocity being approximately 0.5 micrometers/s.
Figure 7:
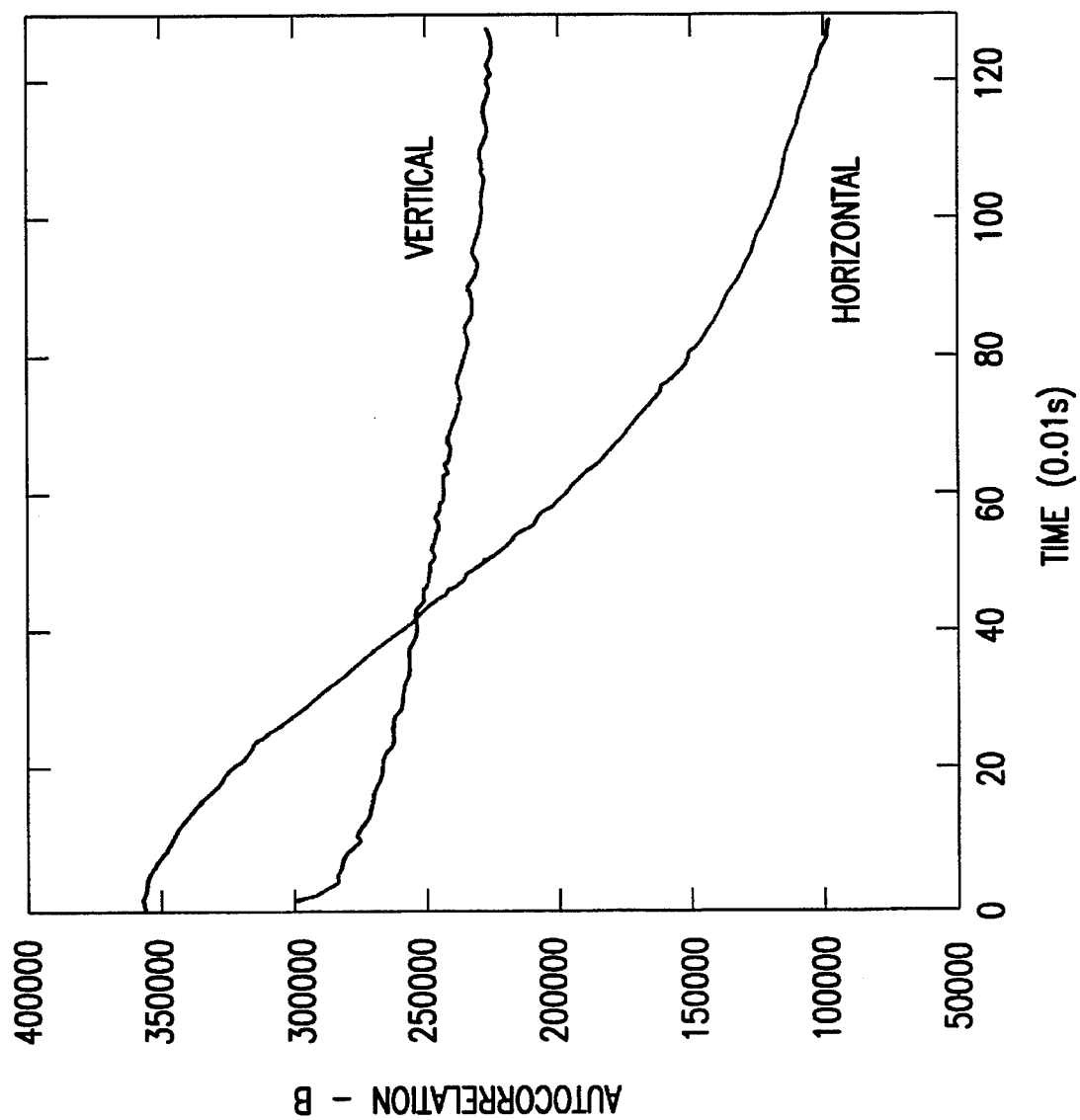
FIG. 7 is the autocorrelation spectra of silver in 0.1M KCN and 0.1M $KAg(CN)_2$ at a potential of −0.1 V measured with the electrode surface oriented vertically and horizontally relative to the surface of the earth.

Light scattered from particles moving with a constant velocity V has an autocorrelation function given by:

$$I_{p1} = \exp(-q^2 Dt) \exp(iqVt)$$

where D is the diffusion coefficient and q is the scattering vector. In the horizontal position of the electrode area, q and V are aligned and oscillations are expected from the periodic term of the last equation. In the vertical position and positive bias, $$Ag + n(CN)^- = Ag(CN)_n^{(n-1)-} + e^-$$

where n may have values 2, 3 or 4. A three-step reaction mechanism was proposed, which involves the adsorbed silver cyanide species of lower valency. According to the reaction mechanism, current in this region is limited by the dissolution of $AgCN_{ad-}$ in the presence of excess cyanide. In addition, the existence of stable silver cyanides is possible in this potential region. Therefore, the observed particles may consist of the above intermediate reaction products. The steep increase of the anodic current, commencing at +0.1 V reflects the formation of the $Ag_2O$. Meanwhile the surface of the electrode turns black. Nevertheless, the autocorrelation spectra, recorded at +0.5 V and 1 V show only quantitative changes, suggesting that the same intermediate anodic reaction product is involved. To verify this point, an attempt was made to determine the diffusivity of particles from the measurements in vertical position (FIG. 7) and therefore to deduce the size. The shape of the two spectra in FIG. 7 suggest a diffusive motion in the vertical case and uniform motion for the horizontal orientation. Hence, the particle density $\rho_p$ could be inferred from the Stokes formula for the velocity:

$$V = 2r^2(\rho_p - \rho_s)g/9\eta$$

where $\eta$ the dynamic viscosity of the solution and $\rho_s$ is the solution density. At $-0.1$ V, the diffusivity was found equal to $10^{-9} cm^2 s^{-1}$ which corresponds to a particle radius of about 4 micrometers. Considering the average velocity measured as shown in FIGS. 5a and 5b, this provides a relative density with respect to that of water of about 1.02. The shape of the spectrum in FIG. 5a is suggestive of a system of particles moving downward with a distribution of velocities. FIG. 5b shows that the average velocity is approximately 0.5 micrometers/s. At more anodic potentials of +0.5 and 1 V the diffusivity values are still smaller (in the range of $10^{-10}$ to $10^{-11}$ cm$^2$s$^{-1}$) leading to larger radii values. These results mean either that the released particles are very porous or that the consistency between the diffusivity and velocity data is not yet clearly established. In fact, the velocity data reveal a broad distribution where large velocities, and therefore large particles may be present. The diffusivity measurements are strongly sensitive to large particles and the use of the average velocity to calculate the density is probably not correct.

Figure 6A:
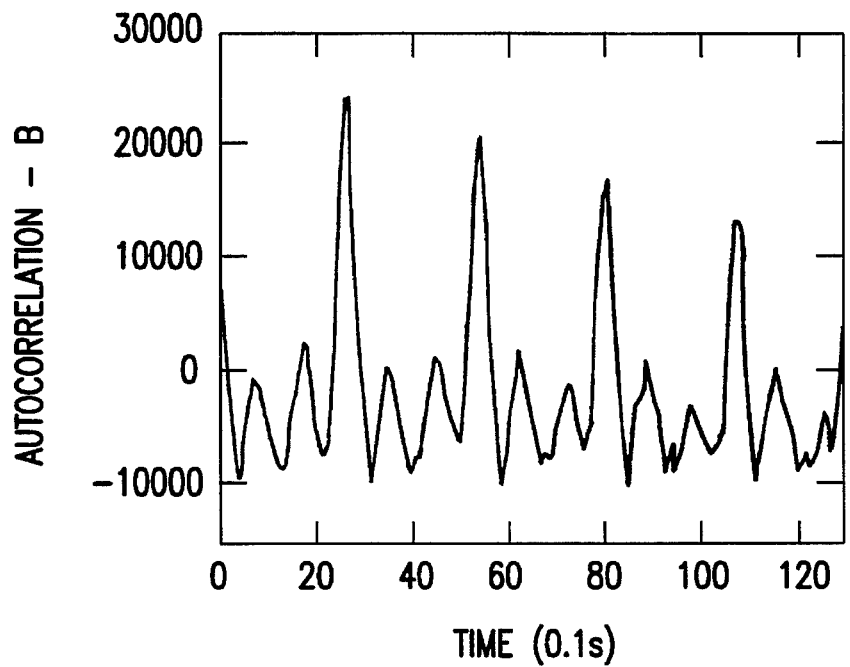
FIG. 6a is the measured autocorrelation spectrum for a silver electrode in a solution containing 0.5M KCN+0.1M $KAg(CN)_2$ at a potential of +1.0 V.
Figure 6B:
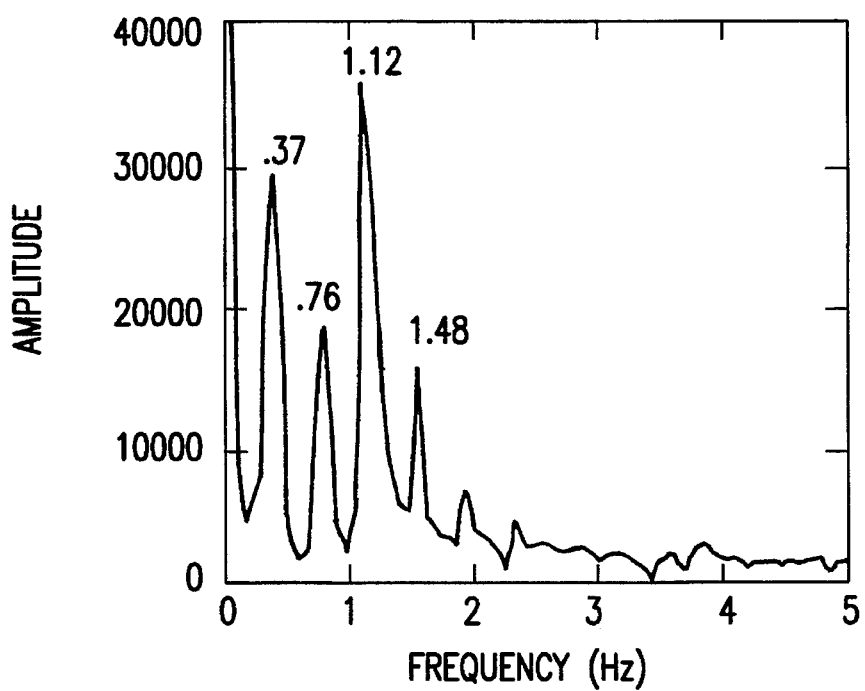
FIG. 6b is the Fourier transform of the spectrum in FIG. 6a, in which most of the large frequency components are harmonics of a fundamental at 0.37 Hz.

Surprisingly, for a higher cyanide concentration of 0.5M, the Fourier transformation of the autocorrelation spectra displayed in FIG. 6a and 6b show very well defined frequencies with harmonics. The large oscillations in FIG. 5a suggest that there may be convective cells near the electrode surface driving the particles. The electrode surface turns black with clearly visible particles. After a while, spatially organized dissolution patterns are formed. It is then most likely that the concentration of particles is enough to induce natural convection with cells of finite dimensions of the Rayleigh-Benard type. In this situation, the particles will move at the same velocity even if they are distributed in size.

Instrumentation

Figure 8:
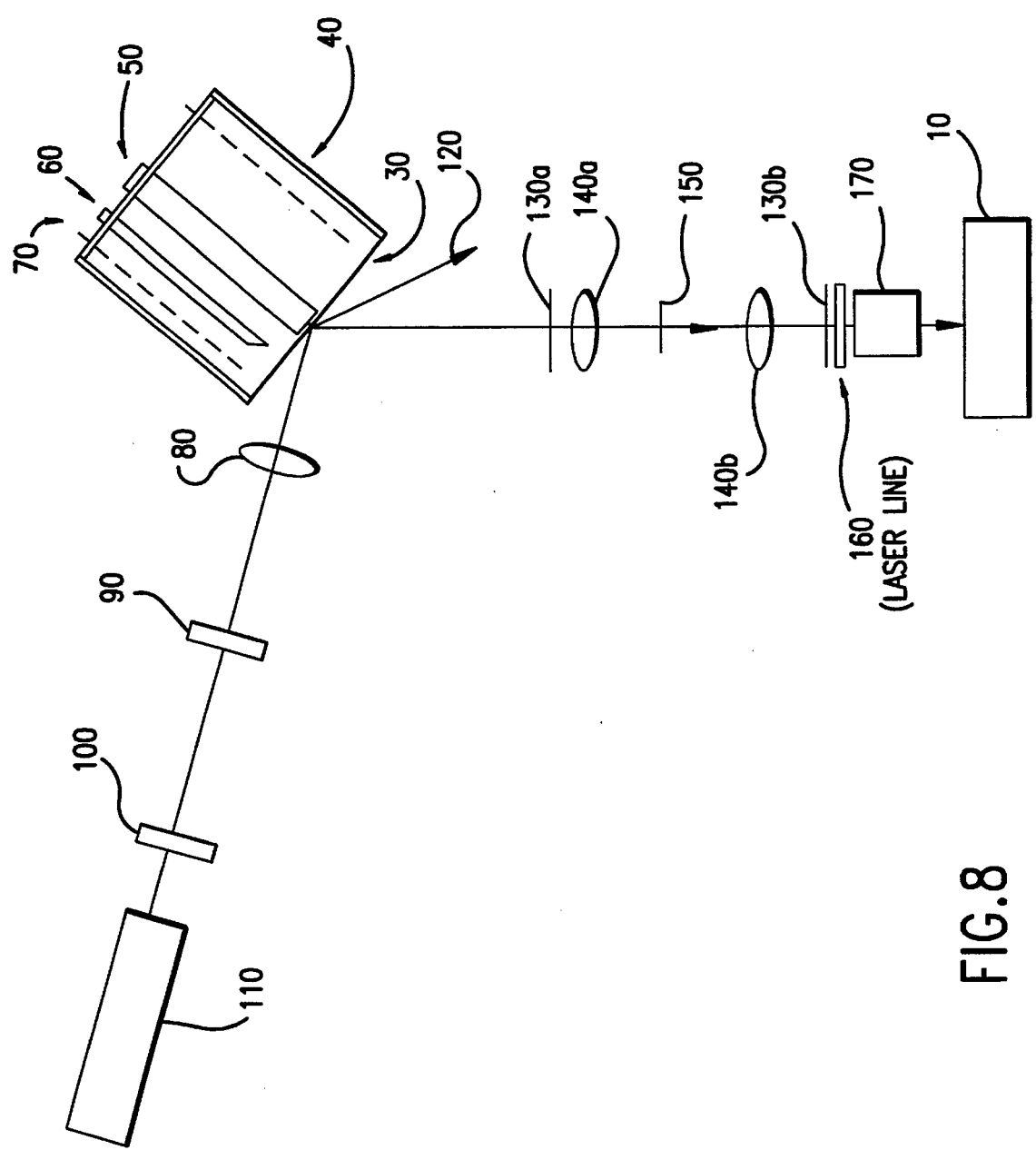
FIG. 8 is a schematic of another apparatus used in the present invention, which measures photon scattering from the electrode surface.

FIG. 8 shows a diagram of the apparatus which was used to implement the surface monitoring technique, in which 30, 40, 50, 60, 70, 80, 90, 100 and 110 are the same as in FIG. 1 and 120 indicates a specular reflection, 130a and b indicate pin holes, 140a and b indicate lenses, 150 indicates a spatial filter, 160 indicates a filter at the laser line and 170 indicates a PMT. There are three basic components: a source of coherent light such as a low power helium-neon or solid state laser which illuminates the electrochemical interface, a detector assembly which counts photons scattered from the interface, and a digital autocorrelator which accumulates a photon autocorrelation function, C(t).

Methodology and theory

The autocorrelation function, C(t), reflects dynamic processes occurring on the interface which change the scattering properties of the interface. As is known in the art, the measured autocorrelation functions, C(t), can be written as follows:

$$C(t) - B = <N>^2 (P_1 \exp(-G_1 t) = P_2 \exp(-G_2 t) = P_3)^2$$

for the case where two independent processes are responsible for modifying the surface scattering properties. The decay coefficients $G_1$ and $G_2$ characterize the evolution of the two processes. The measured values of the G's can be used with a process model to infer the state of the process. Any other autocorrelation function which can accomplish the desired result can also be utilized in the present invention.

Example 1: Dissolution and deposition

Figures 9A, 9B:
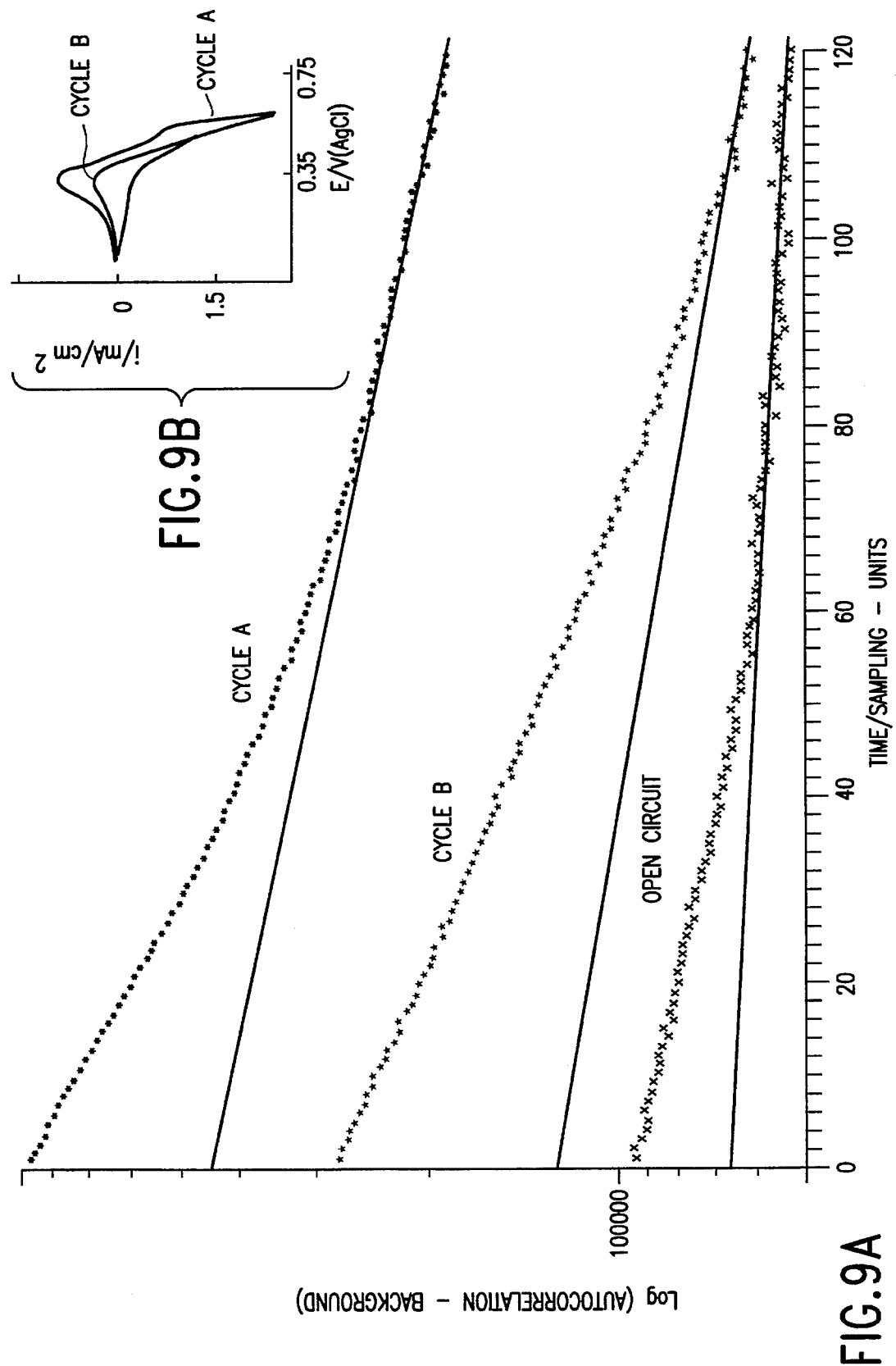
FIG. 9 is a graph showing the autocorrelation function recorded during multiple cycling of the electrode potential of Example 1.

FIG. 9 shows the measured autocorrelation function from a silver surface undergoing dissolution and deposition, in which cycles A and B were over a potential range of 0 to +0.5 V and 0 to +0.6 V, respectively. In both cases, the scan rate was equal to 0.5 V/s and the sampling time was $10^{-4}$ s. The curve denoted by "open circuit" was obtained immediately following cycle A under open circuit conditions. The inset is the polarization curve during the respective cycles. The silver surface is exposed to a solution containing 0.1M $Na_2SO_4 + 0.003M$ KCN at a pH =10.5. There are two decay rates associated with the autocorrelation function. The slow decay parameter, $G_2$, characterizes the decay of surface roughness fluctuations which are in turn correlated to the growth and dissolution rates. The fast decay (with a decay constant $G_1$) is due to insoluble products formed at the silver interface. The parameter $G_1$ leads to an estimate of the particle size. The time required to accumulate the autocorrelation spectrum in FIG. 9 is of the order of seconds. The measurement can be carried out on any metal surface which is undergoing dissolution or deposition.

Example 2: Oxidation and reduction

Figure 10:
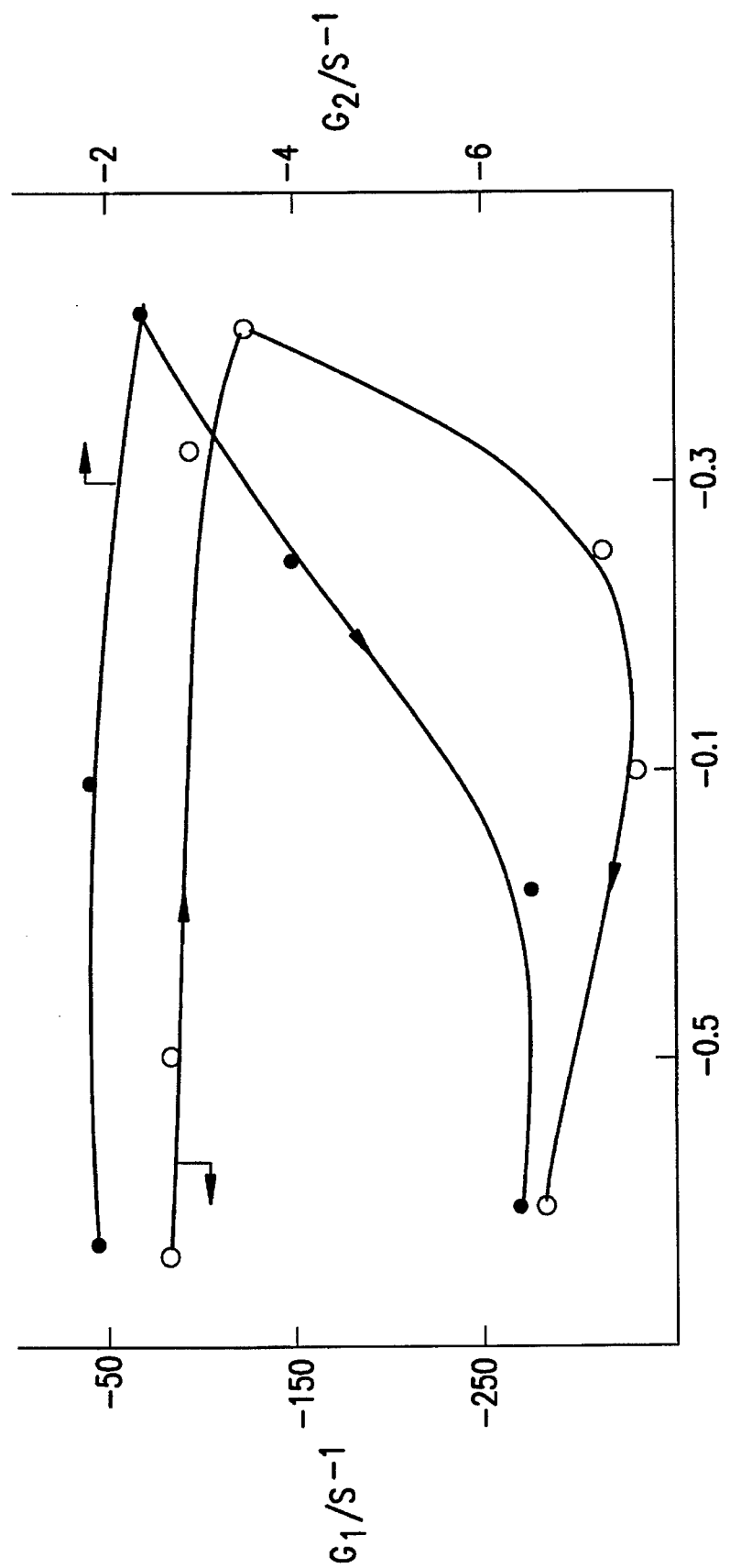
FIG. 10 is a graph of the variation of fast, $G_1$, and slow, $G_2$, decay coefficients of the photon autocorrelation function during the oxidation-reduction cycle, as in Example 2.

FIG. 10 shows the fast, $G_1$, and the slow, $G_2$, decay coefficients of the autocorrelation function measured during oxidation-reduction cycle on a silver surface under conditions which do not lead to insoluble products. The metal is exposed to an aqueous solution containing 0.1M $Na_2SO_4$ at a pH =6.6. The slow decay coefficient characterizes the variation of surface roughness while the fast decay coefficient is a measure of dynamic changes of surface polarizability induced by reaction products. The different magnitudes of the two decay coefficients during oxidation and reduction reflect different surface processes occurring during these times. The autocorrelation spectra were accumulated over a period of 10s. The measurement can be carded out on any surface whose polarizability changes due to chemical reactions. Particles are not produced by these processes.

Example 3: Characterization of particles produced at interfaces

Figure 11:
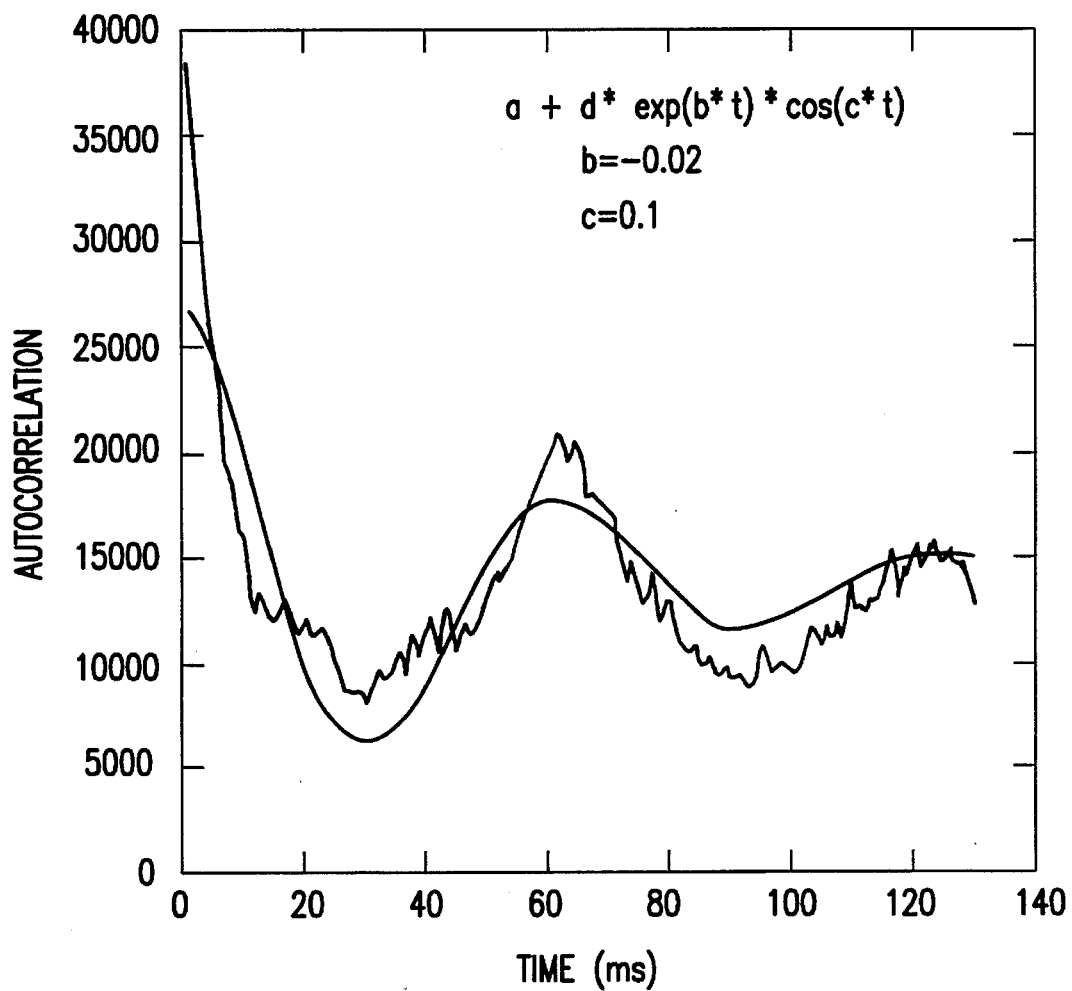
FIG. 11 is a graph of the measured autocorrelation spectrum from particles produced in Example 3.

FIG. 11 shows the measured autocorrelation spectrum of photons scattered from a copper surface under conditions favorable to the formation of insoluble products (submicron particles). The spectrum is from particles produced during potentiostatic dissolution (+0.7 V) of a copper electrode in a solution containing 0.1M $Na_2SO_4$+0.01M KCN at a pH=10.5. The scattering plane was parallel to the direction of gravity. The oscillations in the spectrum are caused by the interference of photons scattered from the moving particles and the stationary copper interface. The frequency of the oscillation gives a particle velocity of approximately 20 micrometers per second. The measurement of the autocorrelation spectrum with the plane of scattering perpendicular to gravity gives the diffusion coefficient of the particles. From these two measured quantities the particle density can be inferred. A fit to an expected response is shown by the continuous line. It is calculated for a particle velocity of 20 micrometers per second.

Comparison of the invention with technical alternatives

Industrial electrochemical processes are monitored by current or potential measurement, weight loss analysis, bath composition analysis and visual inspection of electrodes. Optical techniques such as ellipsometry, reflectometry, second harmonic generation, and surface spectroscopy are useful in the laboratory environment but are of limited practical utility. All of the techniques currently employed in industrial monitoring provide no information about the real time surface condition of the electrode. Since the surface condition determines the successful outcome of the process, real time information on the status of the surface is crucial. The proposed method provides a technique for in situ monitoring of the surface condition.

The invention could be of widespread application in industrial processes where the monitoring of surface condition is critical, such as metal finishing, electrowining and electrolysis of waste water. In the area of heterogeneous catalysis processes the monitoring of catalyst surface can be accomplished using this method. In protein separations of membrane fouling can be accomplished using this method.

This invention may be embodied in other forms or carded out in other ways without departing from the spirit or essential characteristics thereof. This disclosure is therefore, to be considered as in all respects illustrative and not restrictive, the scope of the invention being indicated by the appended claims, and all changes which come within the meaning and range of equivalency are intended to be embraced therein.

What is claimed:

1. A method for the dynamic measurement of the progress of a chemical reaction at an electrochemical interface comprising:

applying a direct coherent light to a solid interface within a sample in which the chemical reaction is occurring;

measuring a scattering of the light after it contacts the interface; and autocorrelating the scattering information with previously obtained scattering information for the solid interface;

wherein the measurement of the progress of the chemical reaction is made in situ.

2. The method of claim 1 wherein the step of applying a direct coherent light comprising applying a direct coherent light from a laser.
3. The method of claim 1 wherein the chemical reaction is metal finishing.
4. The method of claim 1 wherein the chemical reaction is electrochemical machining.
5. The method of claim 1 wherein the chemical reaction is corrosion protection.
6. The method of claim 1 wherein the chemical reaction is metal deposition.
7. The method of claim 1 wherein the chemical reaction is electrochemical production.
8. The method of claim 1 wherein the chemical reaction is waste water treatment.
9. The method of claim 1 wherein the chemical reaction is electrowining.
10. The method of claim 1 wherein the chemical reaction measured is at a solid-liquid interface.
11. The method of claim 1 wherein the chemical reaction measured is at a solid-gas interface.
12. The method of claim 1 wherein the the applying step comprises applying a direct coherent light to an electrode.
13. The method of claim 1 wherein the light has an angle of incidence with respect to the interface that is changed in order to measure different properties of the chemical reaction.
14. The method of claim 1 wherein the progress of the chemical reaction is based on at least one property selected from the group consisting of particle velocity, particle density, particle size and diffusion coefficient of particles involved in the chemical reaction.
15. The method of claim 1 wherein the progress of the chemical reaction is measured by measuring dynamic surface roughness of the solid interface on a time scale of a second and by measuring changes in surface polarizability during the chemical reaction on a time scale of a millisecond.
16. The method of claim 1 wherein a voltage is applied to the solid interface.
17. The method of claim 1 wherein the measured fluctuations are autocorrelated to obtain an autocorrelation spectrum.
18. The method of claim 16 wherein different voltages are applied to the solid interface so that different autocorrelation spectra are obtained.
19. A method for the dynamic measurement of the progress of a chemical reaction at an interface comprising:

applying a direct coherent light to the interface at which the chemical reaction is occurring;

measuring fluctuations of the light intensity after the light is scattered from the interface;

wherein the measured fluctuations of the scattered light intensity are made in situ during the chemical reaction.

20. The method of claim 19 wherein the fluctuations are autocorrelated and an autocorrelation spectrum is obtained.

\* \* \* \* \*